(12) United States Patent
Hara et al.

(10) Patent No.: US 6,821,107 B1
(45) Date of Patent: Nov. 23, 2004

(54) METHOD OF FORMING A STRUCTURE HAVING MULTIPLE CELL LAYERS

(75) Inventors: Masayuki Hara, Ibaraki (JP); Jun Miyake, Ibaraki (JP); Ayako Yamaki, Chiba (JP)

(73) Assignee: Secretary of Agency of Industrial Science and Technology (JP)

( * ) Notice: Subject to any disclaimer, the term of this patent is extended or adjusted under 35 U.S.C. 154(b) by 128 days.

(21) Appl. No.: 09/699,133

(22) Filed: Oct. 27, 2000

(30) Foreign Application Priority Data

Oct. 29, 1999 (JP) .......................................... 11/309684

(51) Int. Cl.$^7$ ............................. C12N 5/06; C12N 5/08; C12N 11/02; C12N 11/10
(52) U.S. Cl. ....................... 425/397; 435/177; 435/178; 435/395; 435/401; 435/402
(58) Field of Search ............................... 435/174, 178, 435/180, 373, 395, 397, 401, 402

(56) References Cited

U.S. PATENT DOCUMENTS 5,976,780 A * 11/1999 Shah ........................... 435/1.1
6,080,579 A * 6/2000 Hanley, Jr. et al. ......... 435/366

FOREIGN PATENT DOCUMENTS

| JP | 05-252952 | 5/1993 |
| JP | 05-000081 | 8/1993 |
| JP | 05-260959 | 12/1993 |

* cited by examiner

*Primary Examiner*—David M. Naff
(74) *Attorney, Agent, or Firm*—Fish & Richardson P.C.

(57) ABSTRACT

Multiple cell layers are formed with one cell layer formed on another cell layer. A carrier is provided having an alginate gel layer formed on a porous membrane. An extracellular matrix component gel layer or extracellular matrix component sponge layer may be formed on the alginate gel layer. A cell layer is formed on the alginate gel layer, or the extracellular matrix component gel layer or extracellular matrix component sponge layer. The alginate gel layer is solubilized such as with a chelating agent to exfoliate the cell layer from the porous membrane, and the exfoliated cell layer is placed on another cell layer on a carrier. The number of cell layers formed on each other may be 1–10, preferably 1–5, and more preferably 1–3.

19 Claims, 3 Drawing Sheets

FIG. 2

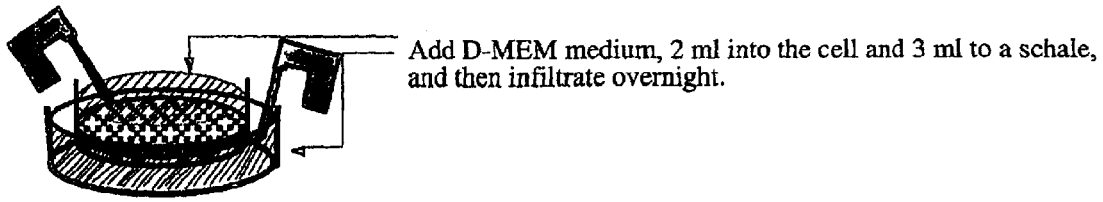

Add D-MEM medium, 2 ml into the cell and 3 ml to a schale, and then infiltrate overnight.

⇩

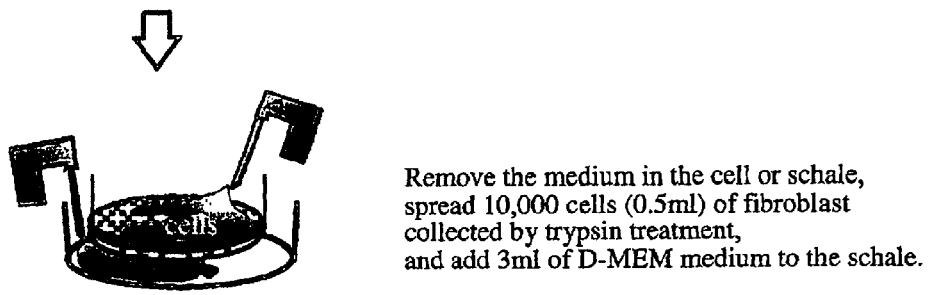

Remove the medium in the cell or schale, spread 10,000 cells (0.5ml) of fibroblast collected by trypsin treatment, and add 3ml of D-MEM medium to the schale.

Leave in a 0.5% $CO_2$ incubator for about 1 hour at 37°C to allow the attachment of fibroblast.

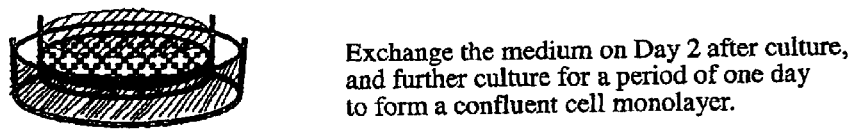

Exchange the medium on Day 2 after culture, and further culture for a period of one day to form a confluent cell monolayer.

⇩

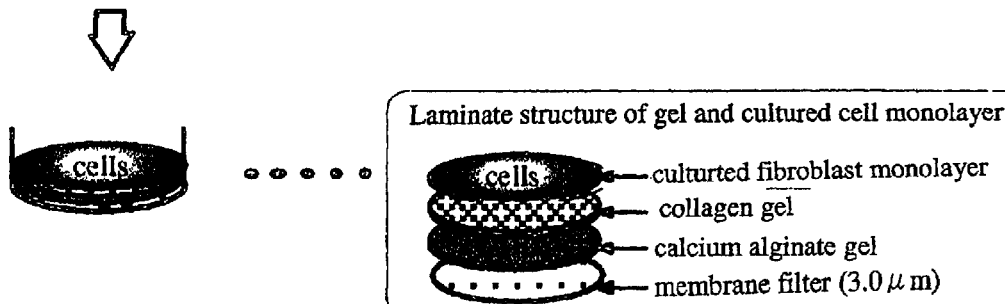

Laminate structure of gel and cultured cell monolayer
— culturted fibroblast monolayer
— collagen gel
— calcium alginate gel
— membrane filter (3.0 μm)

FIG. 3

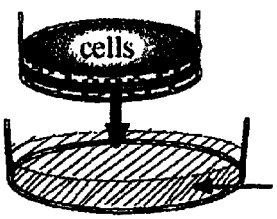

Soak the cell into 0.1M EDTA solution to dissolve the calcium alginate gel and liberate it from the membrane filter

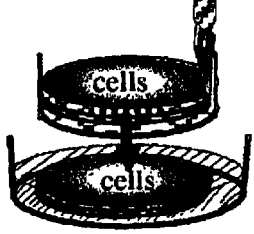

Remove extra water from the cell by suction, insert a scalpel through the inner wall of the cell to hollow the filter, thereby suspending a cell sheet of collagen gel in D-MEM medium.

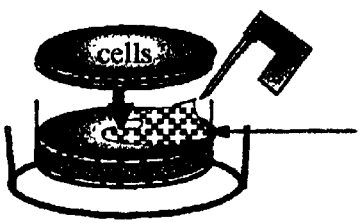

Add 0.5ml of a collagen solution onto the gel sheet which is not suspended, and overlay a gel formed in the same manner as above

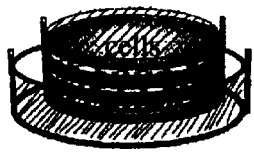

Culture three cell layers laminated with a sandwiched collagen gel, in D-MEM medium.

METHOD OF FORMING A STRUCTURE HAVING MULTIPLE CELL LAYERS

FIELD OF THE INVENTION

The present invention relates to a cell culture technique. More specifically, it relates to a carrier for cell culture, to a method for culturing cells using the carrier, to a cultured cell layer obtained by this method, to a method for piling up another cell layer on the cultured cell layer, and a cell multi-layer obtained by this piling up method.

BACKGROUND OF THE INVENTION

Since hydrated polymer gel has a bio-mimetic structure and has expanding or contracting properties depending on external conditions such as temperature or acidic/alkaline condition, it has been attempted not only to apply such a gel to an artificial organ or tissue such as artificial muscle, and to use it in the medical field for controlling the amount of release of a drug which has been encapsulated within the gel, but also to use it as a support for cell growth being the gel which comprises various types of cytokines or the like.

Among hydrated polymer gels, inter alia N-isopropylacrylamide (referred to as "NIPAM" hereafter), which is a temperature responsive polymer, can swell and is in a liquid state at a low temperature; however, it occurs phase transition at around 34° C. thereby resulting in rapid contraction and gelation.

So far, for the purpose of stratification of cultured cell layers, a method has been used, wherein the cell cultured on NIPAM gel was piled up on another cell layer together with the NIPAM at a temperature of 37° C., subsequently the NIPAM was liquefied by lowering the temperature below 34° C. to be removed, whereby those cells were directly piled up each other.

Generally, when cell is cultured on NIPAM, it grows in the form of a monolayer, forming Extracellular Matrix (referred to as "ECM" hereafter) such as collagen between two adjacent cells. In this case the cell must attach to ECM for its growth.

However, because the upper side of cell layer, as well as the region between the cell and NIPAM (as a basal layer), is not attached to another cell, ECM, which is necessary for cell adhesion, is not formed.

Thus, even if monolayers of cells cultured on NIPAM are piled up each other, and then the NIPAM is removed by solubilizing under temperature conditions below 34° C. to pile up the cell layers so as to be contacted directly each other, the support is not enough for the cell overlaid above to be proliferated, accordingly, stable proliferation could not be expected.

Since the phenomenon is seen that the liquefied NIPAM also acts as cytotoxin to inhibit the normal cell growth, the above method was a very unsuitable and unstable technique as a means of cell stratification.

So far, there was no successful example of culturing a cell on a medium prepared by piling up the ECM component on various types of gels followed by gelation, and establishing a culture system has been attempted, the system employing a medium wherein the gel, no longer required after piling up, can be readily removed.

In those circumstances, the object of the present invention is to provide a technique for piling up cells in a stable and easy manner without using NIPAM which inhibits the cell growth and proliferation when it is solubilized, and a technique wherein cells on upper and lower sides can be adhered to each other via ECM (e.g. collagen) when the cell layers are piled up; that is, the invention is aimed at establishing a technique for the cell multi-layer which has been considered to be difficult to achieve in vitro except certain tissues including skin.

SUMMARY OF THE INVENTION

Alginic acid is a block copolymer composed of glucuronic acid (G) and mannuronic acid (M), wherein glucuronic acid forms an egg-box structure such that it surrounds a multivalent metal ion (e.g. calcium ion), thereby forming an alginate gel (see FIG. 1). The greater the G/M ratio is, the higher the ability of alginic acid to form the gel becomes. However, since the alginate gel can not be molten even at a temperature above 100° C., the method using a temperature sensitive substance like NIPAM is rather inappropriate as a method for exfoliating a living cell from alginate gel. On the other hand, the alginate gel is easily dissolved and liquefied when being soaked in a chelating agent (e.g. EDTA). Additionally, since the alginate gel is a natural product belonging to algae with a property of biodegradability, it does not inhibit the normal cell growth even when the alginate gel is not removed sufficiently upon its dissolution.

As a result of the extensive and intensive studies that were focused on the above properties of alginate gel, the present inventors have now found that it is easy to pile up a cell layer on an another cell layer when a cell is cultured using a carrier which comprises an alginate gel layer (e.g. calcium alginate gel layer) piled up on a porous membrane, followed by solubilizing the alginate gel layer. In this method utilizing the alginate gel, the cell culture containing cell layers can readily be detached.

The present inventors have also found that depending on types of cells to be cultured with the carrier for cell culture, the culture of cells can be carried out more efficiently by using a carrier for cell culture wherein ECM component gel layer (e.g. collagen gel layer) or ECM component sponge layer (e.g. collagen sponge layer) is further piled up on the alginate gel layer which has been piled up on a porous membrane.

The present invention was accomplished on the basis of the above described findings.

Thus, the present invention includes the following inventions:

(1) A carrier for cell culture comprising a porous membrane and an alginate gel layer which is formed on the membrane.

(2) The carrier of (1), wherein the alginate gel layer is composed of a calcium alginate gel.

(3) The carrier of (1) or (2), which further comprises an extracellular matrix component gel layer or extracellular matrix component sponge layer which is formed on the alginate gel layer.

(4) The carrier of (3), wherein the extracellular matrix component is collagen.

(5) A method for culturing a cell, wherein the method comprises culturing the cell using the carrier for cell culture according to any one of (1) to (4).

(6) A method for piling up a cell, wherein the method comprises: forming a cell layer on the carrier according to any one of (1) to (4); solubilizing an alginate gel layer of the carrier thereby exfoliating the cell layer from a porous membrane of the carrier; and piling up the exfoliated cell layer on another cell layer formed on the carrier according to any one of (1) to (4).

(7) A cell multi-layer obtained by the method according to (6).

BRIEF DESCRIPTION OF THE DRAWING

FIG. 2 shows the procedures for culture of cells using the carrier for cell culture.

FIG. 3 shows the procedures for piling up cell layers.

DETAILED DESCRIPTION OF THE INVENTION

Figure 1:
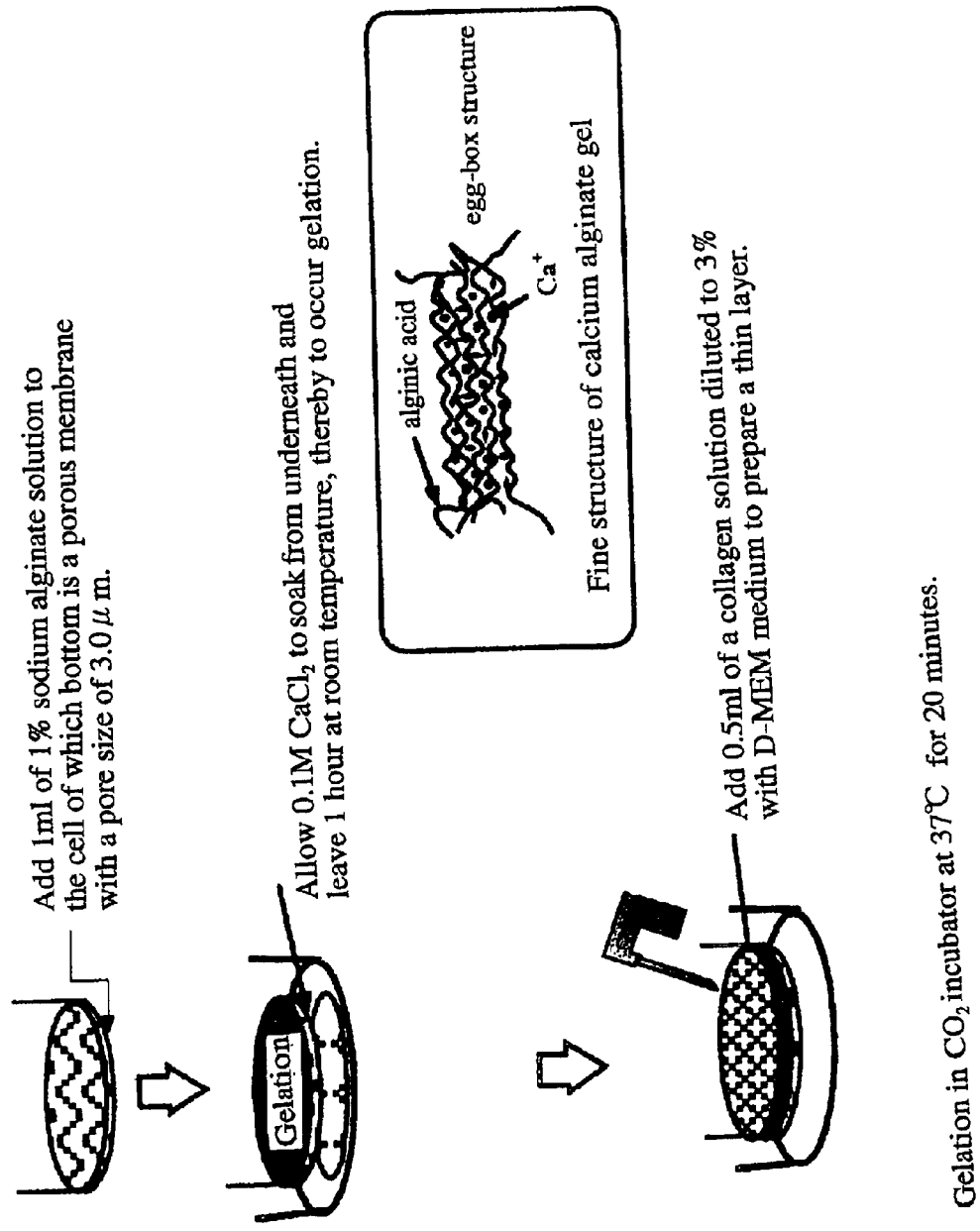
FIG. 1 shows the procedures for preparing a carrier for cell culture.

The present invention will be described in detail.

The carrier for cell culture of the invention is characterized by comprising a porous membrane and an alginate gel layer which is piled up on the membrane.

As used herein, the term "carrier for cell culture" means a carrier or support usable in culturing cells.

The term "porous membrane" as used herein means a membrane through which chelating agent is permeable but alginate gel is not. The "porous membrane" is not limited to particular ones so long as it satisfied the above definition, and it can include, in addition to a membrane with pores, a membrane with inner cavities or a membrane with both pores and inner cavities. Examples of the porous membrane includes a filter, an ultrafiltration membrane, a silicone rubber membrane, a polytetrafluoroethylene resin porous membrane (or PTFE porous membrane), a nonwoven fabric, a gauze-like mesh, and various types of membrane filters, preferably ultrafiltration membrane and hydrophilic PTFE porous membrane. Where the porous membrane has pores, the pore size is, but not limited to, generally 0.02–1000 µm, preferably 0.02–100 µm, more preferably 0.1–10 µm, so far as it is a size capable of permeating a chelating agent not an alginate gel.

As used herein, the term "alginate gel" means an alginate in which the gelation occurs due to formation of a chelate structure from the carboxylate group and multivalent metal ion in alginic acid molecule. The term "alginate gel layer" means a lamellar alginate gel. Alginic acid is a block copolymer composed of guluronic acid (G) and mannuronic acid (M), which is considered to gelate due to information of an egg-box by invasion of a multivalent metal ion into a pocket structure of M block (see FIG. 1). Examples of the multivalent metal ion which can cause gelation of alginic acid include metal ions such as barium (Ba), lead (Pb), cupper (Cu), strontium (Sr), cadmium (Cd), calcium (Ca), zinc (Zn), nickel (Ni), cobalt (Co), manganese (Mn), iron (Fe), and magnesium (Mg) ions, preferably Ca, Mg, Ba, and Sr ions. Gelation of alginic acid can be carried out according to usual methods including, for example, utilization of ionic exchange. For instance, ionic exchange occurs promptly after addition of calcium ion to an aqueous solution of sodium alginate, resulting in production of a calcium alginate gel. More specifically, calcium alginate gel layer can be obtained by adding 0.3–0.5 ml of 0.2–2% sodium alginate solution to the cell of which bottom is porous membrane (e.g. a membrane with pore size of 3.0 µm, manufactured by FALCON), then allowing a solution of 0.01–0.1 M $CaCl_2$ to soak through the porous membrane, and leaving for a period of 0.5–1 hour at a temperature of 20–30° C. Thus, the carrier for cell culture comprising the porous membrane and alginate gel layer piled up thereon can be obtained by gelating alginic acid using the porous membrane. However, in the present invention the gelation of alginic acid using a porous membrane is not essential, and in this case the carrier for cell culture may be prepared by positioning an alginate gel made separately, on a porous membrane.

Alginic acid exists naturally as a cell wall constitutive polysaccharide or intercellular filling material in phaeophyceae, from which alginic acid can be prepared. Example of phaeophyceae used as the raw material include Laminariales Laminaria (e.g. Laminaria japonica Areschoug). Alternatively, commercially available alginic acid may be used. The G/M ratio of alginic acid is not specifically limited to specific ones; however, the greater the G/M ratio is, the higher the ability of alginic acid to form a gel becomes. Thus, the G/M ratio is preferably high. More specifically, it is preferred to be 0.1–1, more preferably 0.2–0.5.

The carrier for cell culture used in the invention may take any structure so far as it comprises a porous membrane and an alginate gel layer piled up thereon. For example, it can take the constitution wherein an ECM component gel layer or ECM component sponge layer is further piled up on the alginate gel layer. If a cell cultured using said carrier for cell culture is more apt to grow/develop on the ECM component gel layer or sponge layer than the alginate gel layer (e.g. fibroblast), it is preferred to pile up the ECM component gel layer or sponge layer on the alginate gel layer.

The term "extracellular matrix component (ECM) gel" as used herein means the gel matter of ECM component, and the term "ECM component gel layer" means a lamellar ECM component gel. The ECM is generally defined as "a stable bio-structure which exists outside the cell in animal tissue, being a complicated assembly of biopolymers extracellularly secreted and accumulated" (Dictionary of Biochemistry ($3^{rd}$ edition) p. 570, Tokyo Kagakudojin, Tokyo, Japan), and it plays roles in supporting cells materially and in regulating activity of cells (i.e. a role for the transduction of extracellular information to cells and the alteration of cellular activity). "Extracellular matrix component" as used herein means a component of extracellular matrix, such as collagen, elastin, proteoglycan, glucosaminoglycan, fibronectin, laminin, or vitronectin, preferably collagen or matrigel (which is a gel composed of collagen type IV, laminin, and heparan sulfate). The ECM components can be obtained by usual methods. Alternatively, commercially available ECM components may be used. The gelation of an ECM component can be carried out in the usual manner. For example, if the ECM component is collagen, then a collagen gel can be obtained by incubating an aqueous solution of 0.3–0.5% collagen at 37° C. for 10–20 minutes. If necessary, a gelling agent may be used in gelation of an ECM component.

As used herein, the term "ECM component sponge" means an ECM component having been processed three-dimensionally into a porous sponge form, and the term "extracellular matrix component sponge layer" means a lamellar ECM component sponge. Since the ECM component sponge itself has a three-dimensional structure, the cell can be cultured in a pile up manner by using the ECM component sponge layer. Impregnating a liposome, which encapsulates various cell growth factors or growth factors therein, into inner vacancies of the ECM component sponge layer also enables cells present within the ECM component sponge layer to induce differentiation without restraint. As for the ECM component, the same examples as mentioned above can be given. The ECM component sponge can be prepared in the usual manner. Commercially available ECM component sponges can also be used.

When the ECM component gel layer is piled up on alginate gel layer, the alginate gel layer and the ECM component gel layer can be piled up after preparing them separately. However, it is preferable to perform gelation of an aqueous solution containing the ECM component after the aqueous solution was overlaid on the alginate gel layer. This is because it is difficult to exfoliate the ECM component gel layer from a container (e.g. dish or scale) in which the ECM component gel layer is formed since the physical strength of the ECM component gel layer is not enough to be detached.

When the ECM component sponge layer is overlaid on the alginate gel layer, it is recommended to pile up the alginate gel layer and ECM component sponge layer after preparing them separately.

The thickness of the porous membrane, alginate gel layer and ECM component gel layer, which constitute the carrier for cell culture of the invention, is not particularly limited, but the thickness of the porous membrane is usually 0.01–1 mm, preferably 0.01–0.1 mm, more preferably 0.05–1 mm, the thickness of the alginate gel layer is usually 0.1–3 mm, preferably 1–2 mm, more preferably 1 mm, the thickness of ECM component gel layer is usually 0.1–1 mm, preferably 0.2–0.5 mm, more preferably 0.4 mm, the thickness of the ECM component sponge layer is usually 0.1–2 mm, preferably 0.2–1 mm, more preferably 0.5 mm.

The size of the carrier for cell culture usable in the invention can be determined appropriately according to for example the number of cells to be cultured, and the carrier can also be molded in an appropriate size by using a scalpel or the like.

The carrier for cell culture in the invention can be used for culturing cells. The culture of cells can be carried out, for example, on alginate gel layer, on ECM component gel layer, or on/in ECM component sponge layer. In the use of the carrier for cell culture composed of a porous membrane and an alginate gel layer piled up on the membrane as the carrier for cell culture of the invention, the cell can be cultured on the alginate gel layer. In the use of the carrier for cell culture further comprising an ECM component gel layer piled up on the alginate gel layer as the carrier for cell culture of the invention, the cell can be cultured on the ECM component gel layer. In the use of the carrier for cell culture further comprising an ECM component sponge layer piled up on the alginate gel layer as the carrier for cell culture of the invention, the cell can be cultured on/in the ECM component sponge layer. Examples of the cell which can be cultured include fibroblast, vascular endothelical cell, chondrocyte, hepatocyte, small intestine epitheliocyte, epidermis cornification cell, osteoblast, and bone marrow mesenchymal cell, preferably fibroblast. When cell is cultured, a culture medium (e.g. D-MEM, MEM, HamF12 or HamF10 medium) with a cell concentration of 10,000–15,000 cells/ml is usually added onto the alginate gel layer, ECM component gel layer, or ECM component sponge layer. The culture conditions of cells can be selected appropriately according to types of cells to be cultured. When cell is cultured on alginate gel layer or ECM component gel layer, the culture is usually continued until confluent cell monolayer is formed on the alginate gel layer or ECM component gel layer.

Specifically, the culture of cells using the carrier for cell culture of the invention can be carried out as follows. The carrier for cell culture is placed in, for example, a schale, and an appropriate culture medium (e.g. D-MEM, MEM, HamF12 or HamF10 medium) is added into the schale, then left for 12–24 hours to soak the culture medium into the carrier for cell culture. The culture medium in the schale is decanted, cells are spread on the alginate gel layer, ECM component gel layer or ECM component sponge layer, and subsequently an appropriate culture medium (e.g. D-MEM, MEM, HamF12 or HamF10 medium) is added into the schale. After leaving 1–2 hours at 37° C. to attach the cell to the alginate gel layer, ECM component gel layer, or ECM component sponge layer, the cell culture is continued at 37° C. During the culture, the culture medium may be exchanged with the same fresh medium if necessary. It is usually exchanged in 0.5–2 day intervals after start of the culture.

The cell culture obtained by the culture of cells using the carrier for cell culture of the invention contains the carrier for cell culture of the invention and the cell layer maintained on the carrier. The "cell layer maintained by the carrier" contains any one of or combination of a cell layer formed on the alginate gel layer, a cell layer formed on the ECM component gel layer, and a cell layer formed on/in the ECM component sponge layer. In the use of the carrier for cell culture composed of a porous membrane and an alginate gel layer piled up thereon as the carrier of the invention, or in the use of the carrier for cell culture further comprising an ECM component gel layer piled up on alginate gel layer as the carrier of the invention, or in the use of the carrier for cell culture further comprising an ECM component sponge layer piled up on alginate gel layer as the carrier of the invention, the cell layer formed in and/or on the ECM component sponge layer corresponds to the "cell layer maintained by the carrier."

The cell culture can be detached from the porous membrane by solubilizing the alginate gel layer. The solubilization of the alginate gel layer can be carried out by use of a chelating agent. Examples of the chelating agent include polyaminocarboxylic acids such as EDTA (ethylenediaminetetraacetic acid) and EGTA (ethylene glycol-bis($\beta$-aminoethyl ether); and oxycarboxylic acids such as citric acid, preferably EDTA and EGTA. The chelating agent can be selected appropriately according to the type of a multivalent metal ion which forms a chelate structure with a carboxylic acid group in the molecule of alginic acid. In the case of calcium alginate gel, for example, EDTA can be used, wherein the concentration of the chelating agent is usually 0.01–1 M, preferably 0.05–0.2 M. The solubilization of the alginate gel layer with a chelating agent is preferably carried out by allowing the chelating agent to soak through the porous membrane. Hereby, the porous membrane and alginate gel layer can be separated easily, and the cell culture can readily be detached from the porous membrane. It is not necessary to completely remove the alginate gel layer by solubilization, and the alginate gel layer incapable of being solubilized may remain. Preferably, the alginate gel layer is removed by solubilizing as much as possible.

Since the cell culture obtained by solubilizing the alginate gel layer contains a cell layer, it can be used for forming cell multi-layer. In forming cell multi-layer, the cell cultures obtained by solubilizing the alginate gel layer may be piled up each other, or one cell culture obtained by solubilizing the alginate gel layer may be piled up on another cell layer prepared separately. The type of cell of a cell layer to be piled up may be the same or different. The number of cell layers to be piled up is, but not limited to, usually 1–10, preferably 1–5, more preferably 1–3.

The cell multi-layer contains any one of or combination of a cell layer formed on alginate gel layer, a cell layer formed on ECM component gel layer, and a cell layer formed on/in the ECM component sponge layer.

Used as the cell layer to be piled up are for example small intestine epitheliocyte layer, muscular layer, and fibroblast layer. By use of such cell layers, the three-dimensional tissue structure of the small intestine wall can be constructed. This three-dimensional tissue structure can be applied as an alternative model for animal experiments or as an internal organ for transplantation, as well as to an in vitro drug permeability test. The cell multi-layer can be cultured under appropriate culture conditions depending on the cell type which composes a cell layer. In culture, a medium such as D-MEM, MEM, HamF12 or HamF10 medium can be used.

EXAMPLES

Example 1

Preparation of Carrier for Cell Culture

The procedures for the preparation of a carrier for cell culture are shown in FIG. 1. Specifically, the carrier was prepared as follows;

(1) One ml of a solution of 1% sodium alginate in water was added to a cell of which bottom is a porous membrane (pore size 3.0 μm; available from FALCON). The porous membrane positioned underneath can permeate water molecule and relatively small molecules, but it cannot permeate macromolecules, such as cultured cells, and polymer gels.

(2) Gelation was performed by allowing 0.1 M $CaCl_2$ to soak through the porous membrane at the bottom of the cell and leaving for 1 hour at room temperature, thereby to prepare a carrier for cell culture that comprises a porous membrane and a calcium alginate gel layer piled up thereon.

(3) 0.5 ml of a 3% collagen solution (collagen type LAC-50, available from Koken, Tokyo, Japan) diluted with D-MEM medium (available from Sigma) was added onto the calcium alginate gel layer to prepare a thin layer of the aqueous collagen solution, followed by incubation for about 20 minutes at 37° C. in a $CO_2$ incubator, thereby resulting in gelation of the collagen solution. By this means, the carrier for cell culture wherein the collagen gel layer was piled up on the calcium alginate gel layer, was obtained.

Example 2

Cell Culture using the Carrier for Cell Culture

The procedures for the culture of a cell using the carrier for cell culture are shown in FIG.2. Specifically, the cell culture was carried out as follows.

(1) After placing the carrier for cell culture prepared in Example 1 along with the cell into a schale, D-MEM medium was added in the amount of 2 ml into the cell and in the amount of 3 ml into the schale, then left overnight in order to allow the D-MEM medium to soak into the carrier for cell culture, (2) Fibroblast cultured in advance was collected by trypsin treatment, and the cell concentration was adjusted to 20,000 cells/ml. After removing the cell and the medium inside the schale, 0.5 ml of the cultured fibroblast (where the number of cells is 10,000) was added onto the collagen gel layer, and 3 ml of D-MEM medium was added into the schale, (3) After incubating for 1 hour at 37° C. in a $CO_2$ incubator, the fibroblast was attached and retained on the collagen gel layer, (4) The medium was exchanged with the fresh one on Day 2 after culture, and the confluent cell monolayer was formed following culture of one more day. As a result, the cell culture which comprises a porous membrane, a calcium alginate gel layer piled up on the porous membrane, a collagen gel layer piled up on the calcium alginate gel layer, and a fibroblast layer formed on the collagen gel layer, was obtained (see FIG. 2).

Example 3

Piling Up Cell Layer

The procedures for piling up a cell layer are shown in FIG. 3. Specifically, they were performed as follows.

(1) The cell culture obtained in Example 2 along with the cell was soaked in the 0.1 M EDTA solution, then EDTA was permeated through the porous membrane to dissolve the calcium alginate gel. By this means, the cell culture comprising the fibroblast layer could be detached from the porous membrane.

(2) An excess of water was removed by suction, and a scalpel was inserted through the inner wall of the cell to hollow out the porous membrane, whereby the cell culture containing the fibroblast layer was suspended in D-MEM medium.

(3) The cell culture containing this fibroblast was piled up on another cell culture obtained in the same manner as in Example 2. By repeating the same operations, piled up cell layers (consisting of 3 layers) were obtained.

(4) It was confirmed that the piled up cell layers could be cultured in D-MEM medium.

As demonstrated by the above described examples, according to the present invention there is provided a carrier for cell culture capable of piling up cell layers easily.

What is claimed is:

1. A method for forming a structure having multiple cell layers comprising:

(a) forming a cell layer on a carrier, wherein the carrier comprises a porous membrane and an alginate gel layer which is formed on the porous membrane, wherein the cell layer is on the alginate layer, or on an extracellular matrix component gel layer or an extracellular matrix component sponge layer which is formed on the alginate gel layer;

(b) solubilizing the alginate gel layer of the carrier thereby exfoliating the cell layer from the porous membrane of the carrier; and (c) placing the exfoliated cell layer on another cell layer formed on a carrier.

2. The method of claim 1, wherein the alginate gel layer is composed of a calcium alginate gel.

3. The method of claim 1, wherein the cell layer is on the extracellular matrix component gel layer or extracellular matrix component sponge layer.

4. The method of claim 1, wherein the extracellular matrix component gel or sponge layer comprises a collagen.

5. The method of claim 1, wherein the porous membrane comprises a filter, an ultrafiltration membrane, a silicone rubber membrane, a polytetrafluoroethylene resin porous membrane, a nonwoven fabric or a gauze-like mesh.

6. The method of claim 1, wherein the membrane has pores that are between about 0.02 to 1000 μm.

7. The method of claim 3, wherein the extracellular matrix component gel or sponge layer comprises a collagen, an elastin, a proteoglycan, a glucosaminoglycan, a fibronectin, a laminin, a vitronectin or a heparan sulfate.

8. The method of claim 3, wherein the extracellular matrix component comprises a gel comprising collagen type IV, laminin and heparan sulfate.

9. The method of claim 1, wherein the thickness of the porous membrane is between about 0.01 to 1 mm, 0.01 to 0.1 mm, or 0.05 to 1 mm.

10. The method of claim 1, wherein the thickness of the alginate gel layer is between about 0.1 to 3 mm or between about 1 to 2 mm.

11. The method of claim 3, wherein the thickness of the extracellular matrix component gel layer is between about 0.1 to 1 mm or between about 0.2 to 0.5 mm.

12. The method of claim 3, wherein the thickness of the extracellular matrix component sponge layer is between about 0.1 to 2 mm or between about 0.2 to 1 mm.

13. The method of claim 1, wherein the cell is a fibroblast, a vascular endothelial cell, a chondrocyte, a hepatocyte, a small intestine epitheliocyte, an epidermis cornification cell, an osteoblast, a bone marrow mesenchymal cell or a fibroblast.

14. The method of claim 1, wherein when forming the cell layer a cell concentration of between about 10,000 to 15,000 cells/ml is added onto the alginate gel layer or the extracellular matrix component gel layer or extracellular matrix component sponge layer.

15. The method of claim 14, wherein solubilization of the alginate gel layer is carried out by use of a chelating agent.

16. The method of claim 15, wherein the chelating agent comprises a polyaminocarboxylic acid, an ethylenediaminetetraacetic acid, an ethylene glycol-bis($\beta$-aminoethyl ether), an oxycarboxylic acids, or a citric acid.

17. The method of claim 10, wherein the thickness of the alginate gel layer is about 1 mm.

18. The method of claim 11, wherein the thickness of the extracellular matrix component gel layer is about 0.4 mm.

19. The method of claim 12, wherein the thickness of the extracellular matrix component sponge layer is about 0.5 mm.

* * * * *